US006979676B2

(12) United States Patent
Sato et al.

(10) Patent No.: US 6,979,676 B2
(45) Date of Patent: Dec. 27, 2005

(54) PHARMACEUTICAL COMPOSITION CONTAINING AND INDOLOPYRROLOCARBAZOLE DERIVATIVE

(75) Inventors: Yuichi Sato, Menuma (JP); David T. Breslin, Drexel Hill, PA (US); Shyam B. Karki, Lansdale, PA (US)

(73) Assignees: Merck & Co., Inc., Rahway, NJ (US); Banyu Pharmaceutical Co., Ltd., Tokyo (JP)

( * ) Notice: Subject to any disclaimer, the term of this patent is extended or adjusted under 35 U.S.C. 154(b) by 205 days.

(21) Appl. No.: 10/255,790

(22) Filed: Sep. 26, 2002

(65) Prior Publication Data

US 2004/0029821 A1    Feb. 12, 2004

Related U.S. Application Data

(60) Provisional application No. 60/402,406, filed on Aug. 9, 2002.

(51) Int. Cl.$^7$ .......................... A01N 43/04; A61K 31/70
(52) U.S. Cl. .......................... 514/43; 514/27; 536/17.7; 536/18.7; 536/27.1; 536/29.1
(58) Field of Search .............................. 536/17.7, 18.7, 536/27.1, 29.1; 514/27, 43

(56) References Cited

U.S. PATENT DOCUMENTS

| | | | |
|---|---|---|---|
| 5,437,996 A | 8/1995 | Kojiri et al. | |
| 5,589,365 A | 12/1996 | Kojiri et al. | |
| 5,591,842 A | 1/1997 | Kojiri et al. | |
| 5,668,271 A | 9/1997 | Kojiri et al. | |
| 5,804,564 A * | 9/1998 | Kojiri et al. | 514/27 |
| 5,922,860 A | 7/1999 | Kojiri et al. | |
| 6,359,130 B1 * | 3/2002 | Singh et al. | 540/546 |

FOREIGN PATENT DOCUMENTS

| | | |
|---|---|---|
| EP | 0 602 597 A2 | 6/1994 |
| EP | 0 545 195 B1 | 11/1995 |

OTHER PUBLICATIONS

Byron Long, et al., Exp. Opin. Ther. Pat. (2000) 10(5) 635-666.

Mitsuru Ohkubo, et al., Bioorg. Med. Chem. Lett. 10(2000) 419-422.
David E. Zembower, et al., Bioorg. Med. Chem. Lett. 9(1999) 145-150.
Michelle Prudhomme, Curr. Med. Chem. 7(2000) 1189-1212.
Mitsuru Ohkubo, et al., Bioorg. Med. Chem. Lett. 9(1999) 3307-3312.
Mitsuru Ohkubo, et al., Tetrahedron, vol. 52, No. 24, pp. 8099-8112 (1996).
Frank Seela, et al., J. Org. Chem. 47(1982) 226-230.
Frank Seela, et al., J. Chem. Soc. Perkin Trans. 1(1988) 697-702.
Helmut Rosemeyer et al., J. Org. Chem. 52(1987) 5136-5143.
Frank Seela, et al., Synthesis (1990) 945-950.
A. Barco, et al., Synthesis (1976) 124-125.
V. Bocchi, et al., Synthesis (1976) 414-416.
N. I. Ghali, et al., J. Org. Chem. 46(1981) 5413-5414.
Rene Csuk, et al., Tetrahedron 55(1999) 739-750.
Eric J. Gilbert, et al., J. Org. Chem. 64(1999) 5670-5676.
Katherine Stott, et al., J. Am. Chem. Soc. 117(1995) 4199-4200.
Alessandro Granata, et al., Carbohydrate Research 86(1980) 305-308.
Mitsuru Ohkubo, et al., Tetrahedron, vol. 53, No. 2, pp. 585-592 (1997).
Atsushi Akao, et al., Tetrahedron 57(2001) 8917-8923.
David Breslin, et al., Abstract from Banyu Symposium, Kinetic and Mechanistic Investigation of Bis-indolocarbazole, a Topoisomerase I Inhibitor, Sep. 14, 2001.
David Breslin, et al., Poster from Banyu Symposium, Kinetic and Mechanistic Investigation of Indolocarbazole, a Topoisomerase I Inhibitor, Sep. 14, 2001.

* cited by examiner

*Primary Examiner*—Richard L. Raymond
*Assistant Examiner*—Patrick Lewis
(74) *Attorney, Agent, or Firm*—David A. Muthard; Mark R. Daniel

(57) ABSTRACT

The present invention is directed to a pharmaceutical composition comprising a compound of Formula I dissolved in propylene glycol and water. The present invention also relates to a pharmaceutical composition containing a compound of Formula I dissolved in propylene glycol and a buffer that has a pH between about 3 and about 5.

6 Claims, No Drawings

PHARMACEUTICAL COMPOSITION CONTAINING AND INDOLOPYRROLOCARBAZOLE DERIVATIVE

This Application claims the benefit of Provisional Application No. 60/402,406, filed Aug. 09, 2002.

BACKGROUND OF THE INVENTION

In the field of cancer chemotherapy, a large number of compounds have already been put to practical use as antitumor agents. However, their activities against various types of tumors are not necessarily satisfactory, and the problems of tolerance of tumor cells to these antitumor agents complicate their clinical use.

Under these circumstances, the development of novel antitumor substances is invariably desired in the field of cancer therapy. Particularly, there is a need for substances which overcome the problem of tolerance to the previously existing antitumor substances and which exhibit efficacy against such types of cancers that they cannot have any sufficient effect on.

Indolopyrrolocarbazole derivatives having excellent antitumor activity are described in several patents, including U.S. Pat. Nos. 5,591,842 and 5,922,860. Among these indolopyrrolocarbazole derivatives, a compound of Formula I:

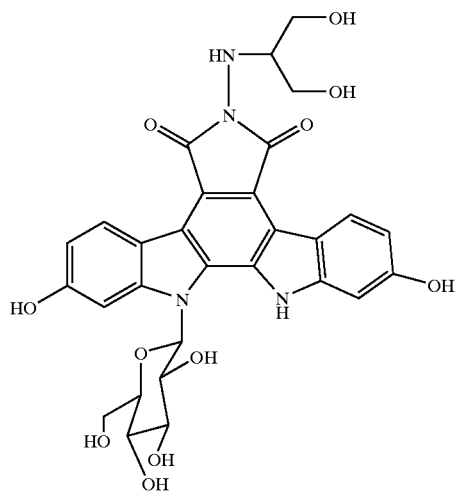

has superior advantages over antitumor agents previously used in terms of activities and safety and therefore its practical use is highly expected. However, the solubility of this compound in water is not optimal.

It is therefore an object of the instant invention to provide a means for improving the solubility and stability of a clinical formulation comprising the compound of Formula I as an active ingredient.

SUMMARY OF THE INVENTION

The present invention is directed to a pharmaceutical composition comprising a compound of Formula I dissolved in propylene glycol and water. The present invention also relates to a pharmaceutical composition containing a compound of Formula I dissolved in propylene glycol and a buffer that has a pH between about 3 and about 5.

DETAILED DESCRIPTION OF THE INVENTION

In a first embodiment, the present invention relates to a pharmaceutical composition comprising a compound of Formula I:

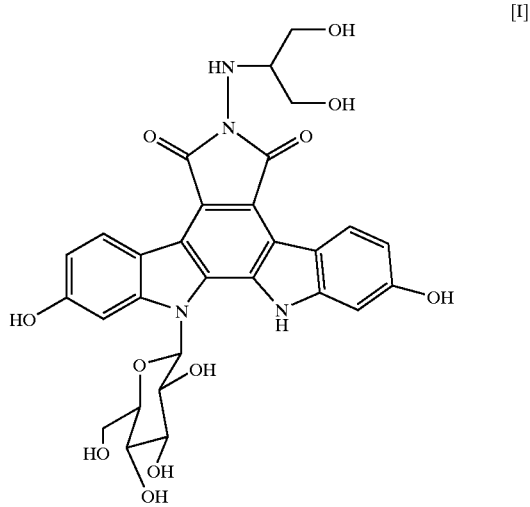

dissolved in propylene glycol and water. The chemical name of the compound of Formula I is 12,13-dihydro-2,10-dihydroxy-6-N-(1-hydroxymethyl-2-hydroxyethylamino)-13-(β-D-glucopyranosyl)-5H-indolo[2,3-a]pyrrolo[3,4-c] carbazole-5,7(6H)-dione. The percentage of propylene glycol in the pharmaceutical composition of the instant invention is preferably between about 40% and about 75% (w/v), more preferably about 50% (w/v).

In a second embodiment, the present invention also relates to a pharmaceutical composition containing a compound of Formula I dissolved in propylene glycol and a buffer that has a pH between about 3 and about 5. The percentage of propylene glycol in the instant invention is preferably between about 40% and about 75% (w/v), more preferably about 50% (w/v).

Preferably, the buffer utilized in the second embodiment is selected from a solution of sodium acetate/acetic acid, sodium citrate/citric acid, tartaric acid/sodium hydrogentartrate, phosphoric acid/sodium dihydrogenphosphate, and phosphoric acid/potassium dihydrogenphosphate. More preferably, the buffer is sodium citrate/citric acid. Preferably, the pH of the buffer utilized is about 4.

In a further embodiment of the second embodiment, the present invention relates to a pharmaceutical composition comprising the compound of Formula I, propylene glycol, and a buffer, wherein the content of propylene glycol is between about 40 and about 75% (w/v), and the pH of the buffer is between about 3 and about 5. More preferably, the content of propylene glycol is about 50% (w/v), the buffer is sodium citrate/citric acid, and the pH of the buffer is about 4.

The present invention encompasses a method of treating cancer in a mammal in need of such treatment which is comprised of intravenously administering to said mammal a therapeutically effective amount of a claimed composition.

Preferably, the method of treating cancer in a mammal in need of such treatment which is comprised of intravenously administering to said mammal a therapeutically effective amount of a composition which comprises the compound of Formula I, propylene glycol, and a buffer, wherein the content of propylene glycol is between about 40 and about 75% (w/v), and pH of the buffer is between about 3 and about 5.

The compound of Formula I that is used in the present invention can be prepared by the methods described in U.S. Pat. No. 5,591,842, which is herein incorporated by reference. Propylene glycol and the ingredients of the respective buffer are commercially available.

The pharmaceutical composition of the present invention may be prepared not only in previously dissolved form, but also in the form of a solution to be further dissolved with suitable solvent(s) or diluent(s) prior to use. The solvents or diluents that may be employed to further dissolve the instant composition prior to use includes, but is not limited to, distilled water for injection, an aqueous solution of lidocaine hydrochloride, physiological saline, an aqueous solution of glucose, ethanol, polyethylene glycol, propylene glycol, liquids for intravenous injection (e.g., an aqueous solution of citric acid and sodium citrate) and an electrolyte solution (for an intravenous drip infusion and an intravenous injection) and so on, as well as mixtures thereof.

The present invention improves the solubility and stability of the compound of Formula I, as seen below in Tables 1, 2 and 3.

TABLE 1

Solubility data of Formula I in various vehicles

| Composition of solvent | Solubility of Formula I (mg/mL) |
| --- | --- |
| 100% PEG 400 | <0.67 |
| 75% PEG 400/water | 24 |
| 50% PEG 400/water | 25 |
| 25% PEG 400/water | 16 |
| 100% PG | 1.2 |
| 75% PG/water | 45 |
| 50% PG/water | 24 |
| 40% PG/water | 12 |
| 25% PG/water | 4.0 |
| water | 0.62 |
| 50% PG/50 mM citrate buffer (pH = 3) | 24 |
| 50% PG/50 mM citrate buffer (pH = 4) | 25 |
| 50% PG/50 mM citrate buffer (pH = 5) | 26 |
| 50% PG/50 mM citrate buffer (pH = 6) | 27 |
| 50% PG/50 mM citrate buffer (pH = 7) | 27 |
| 5% glucose/water | 0.60 |
| 50 mM citrate buffer (pH = 3) | 0.92 |
| 50 mM citrate buffer (pH = 4) | 0.81 |
| 50 mM citrate buffer (pH = 5) | 0.72 |
| 50 mM citrate buffer (pH = 6) | 0.72 |
| 50 mM citrate buffer (pH = 7) | 0.67 |

Notes:
1) Solubility data at room temperature after 1 day.
2) PEG and PG stand for polyethylene glycol and propylene glycol, respectively.
3) % stands for w/v %.

TABLE 2

Stability data of Formula I in various vehicles

| Composition of solvent | Solubility of Formula I (mg/mL) | Stability of Formula I |
| --- | --- | --- |
| 50% PEG 400/water | 10 | −2.9% |
| 50% PG/water | 10 | −0.03% |
| 5% glucose | 0.15 | −0.68% |

Notes:
1) Stability data regarding the purity of the compound of Formula I was obtained by High Performance Liquid Chromatography at initial point and 40° C./1 month.
2) PEG and PG stand for polyethylene glycol and propylene glycol, respectively.

TABLE 3

Degradation rate of Formula I in various pH conditions

| pH | $T_{90}$ |
| --- | --- |
| 10 | 1.2 min. |
| 9 | 7.0 min. |
| 8 | 28 min. |
| 7 | 5.6 hours |
| 6 | 2.3 days |
| 5 | 7.8 days |
| 4 | 89 days |
| 3 | 19 days |
| 2 | 0.9 days |

Note:
$T_{90}$ stands for the time required to degrade Formula I to 90% of the initial concentration at 80° C. pH = 3, 4, and 5 are extrapolated data.

As shown in Tables 1 and 2, as compared with polyethylene glycol (PEG) and 5% glucose solution, it can be said that a pharmaceutical composition comprising about 40 to about 75% (w/v) of propylene glycol and an buffer that has a pH between about 3 and about 5 improves both the solubility and the stability of the compound of Formula I. As shown in Table 3, when the pH of the buffer is about 4, the stability of the compound of Formula I is particularly improved.

When comparing the case of water and that of citrate buffer in Table 4, the citrate buffer preferably improves the stability of the compound of Formula I.

TABLE 4

Stability data of Formula I in PG/water or PG/buffers

| Composition of solvent | Stability of Formula I |
| --- | --- |
| 50% PG/water | −9.3% |
| 50% PG/75 mM citrate buffer (pH = 3) | −2.4% |
| 50% PG/75 mM citrate buffer (pH = 4) | −2.2% |
| 50% PG/75 mM citrate buffer (pH = 5) | −2.9% |

Notes:
1) Stability data were purity of Formula I obtained by High Performance Liquid Chromatography at initial point and 80° C./4 days.
2) PG stands for propylene glycol.
3) All the concentrations of Formula I tested are 5 mg/mL.

TABLE 5

Stability data of Formula I in various PG/buffer solutions

| Composition of solvent | Stability of Formula I |
|---|---|
| 50% PG/water | −30.68% |
| 50% PG/50 mM citrate buffer (pH = 4) | −5.50% |
| 50% PG/50 mM tartrate buffer (pH = 4) | −6.12% |
| 50% PG/75 mM citrate buffer (pH = 4) | −6.49% |

Notes:
1) Stability data were purity of Formula I obtained by High Performance Liquid Chromatography at initial point and 80° C./8 days.
2) PG stands for propylene glycol.

Therefore, the advantageous effect of the present invention is deemed to be an improvement in the solubility and stability of the compound of Formula I, which is caused by dissolving it with propylene glycol and water, or propylene glycol and a buffer that has a pH between about 3 and about 5.

EXAMPLES

Examples provided are intended to assist in a further understanding of the invention. Particular materials employed, species and conditions are intended to be illustrative of the invention and not limiting of the reasonable scope thereof.

Example 1

Preparation of Pharmaceutical Composition Containing a Compound of Formula I

Citric acid, anhydrous (56.7 g) (USP), and 60.3 g of sodium citrate, dihydrate (USP), were dissolved in 4.5 L of water. A solution of 1 N aqueous sodium hydroxide was prepared by dissolution of sodium hydroxide (NF) in water, or diluted hydrochloric acid (NF). This solution was added until the target pH of 4.0 was achieved. Next, 5 kg of propylene glycol (USP) was added to the resultant solution and mixed. 50 g of the compound of Formula I was added to the resultant solution and mixed until it dissolved. The resultant solution was adjusted to 10 L, with water, and mixed. The resultant solution was filtered in a sterile environment through a 0.22 micron filter and subdivided into sterile USP Type I glass vials. The vials were then stoppered with sterile rubber closures and capped with an aluminum crimp seal. The drug product was heated, using an suitable autoclave, as necessary.

Example 2

Preparation of Pharmaceutical Composition Containing a Compound of Formula I 46.7 grams water in a 100 mL volumetric flask was weighed. Next, 0.603 grams (2.05 mmoles) of sodium citrate dihydrate was added and mixed until dissolved. Citric acid monohydrate (0.620 grams, 2.95 mmoles) was added and mixed until dissolved. The pH of the solution was measured. NaOH or HCl was added, depending on adjustment needed to achieve a pH of 4 was achieved. Next, 50 grams of propylene glycol was added and mixed. The compound of Formula 1 (0.5 grams) was added and mixed until it was dissolved. Dissolution took 1 hour with magnetic stirrer. Water was then added to 100 mL volume mark.

What is claimed is:

1. A pharmaceutical composition comprising a compound of Formula I:

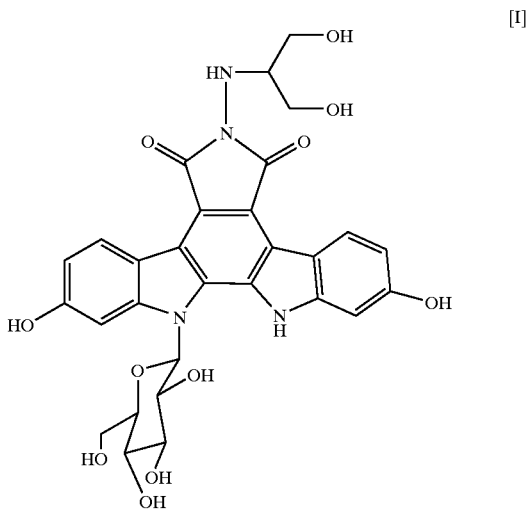

dissolved in propylene glycol and water, wherein the percentage of the propylene glycol in the pharmaceutical composition is between about 40% and about 75% (w/v).

2. A pharmaceutical composition comprising a compound of Formula I:

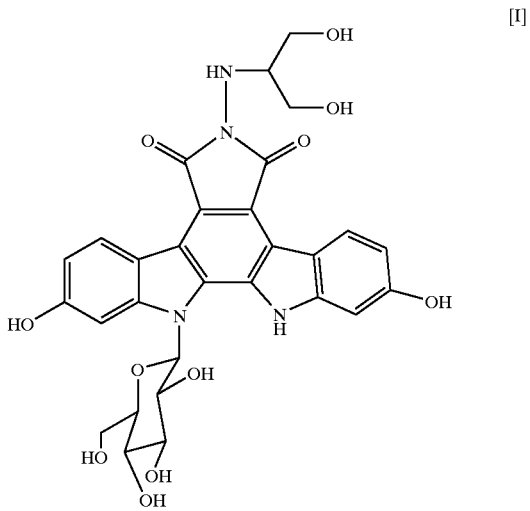

dissolved in propylene glycol and a buffer that has a pH between about 3 and about 5 wherein the percentage of the propylene glycol in the pharmaceutical composition is between about 40% and about 75% (w/v).

3. The pharmaceutical composition according to claim 2, wherein the buffer is selected from sodium acetate/acetic acid, sodium citrate/citric acid, tartaric acid/sodium hydrogen tartrate, phosphoric acid/sodium dihydrogenphosphate, and phosphoric acid/potassium dihydrogenphosphate.

4. The pharmaceutical composition according to claim 3, wherein the buffer utilized has a pH is about 4.

5. The pharmaceutical composition according to claim 4, wherein the buffer is sodium citrate/citric acid.

6. The pharmaceutical composition according to claim 2, wherein the percentage of the propylene glycol in the pharmaceutical composition is about 50% (w/v), the buffer is sodium citrate/citric acid, and the pH of the buffer is about 4.

* * * * *

UNITED STATES PATENT AND TRADEMARK OFFICE
CERTIFICATE OF CORRECTION

PATENT NO. : 6,979,676 B2  
APPLICATION NO. : 10/255790  
DATED : December 27, 2005  
INVENTOR(S) : Yuichi Sato, David T. Breslin and Shyam B. Karki It is certified that error appears in the above-identified patent and that said Letters Patent is hereby corrected as shown below:

On the cover page, section (54) and col. 1, Title of Invention should read:

-- (54) PHARMACEUTICAL COMPOSITION CONTAINING AN INDOLOPYRROLOCARBAZOLE DERIVATIVE --

Signed and Sealed this

Thirty-first Day of October, 2006

JON W. DUDAS  
*Director of the United States Patent and Trademark Office*